US012616692B2

(12) United States Patent
Daly et al.

(10) Patent No.: US 12,616,692 B2
(45) Date of Patent: May 5, 2026

(54) METHOD OF ACHIEVING HIV VIRAL REMISSION USING LONG-ACTING ANTIRETROVIRAL AGENTS

(71) Applicants:ViiV Healthcare Company, Wilmington, DE (US); The United States of America, as represented by The Secretary, Department of Health and Human Services, Bethesda, MD (US)

(72) Inventors: Michele B. Daly, Collegeville, PA (US); Jose Gerardo Garcia Lerma, Collegeville, PA (US); Walid M. Heneine, Atlanta, GA (US); William Robert Spreen, Collegeville, PA (US); Peter Evan Owen Williams, Beerse (BE)

(73) Assignees: ViiV Healthcare Company; and, Wilmington, DE (US); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 599 days.

(21) Appl. No.: 18/002,494

(22) PCT Filed: Jun. 30, 2021

(86) PCT No.: PCT/IB2021/055874
§ 371 (c)(1),
(2) Date: Dec. 20, 2022

(87) PCT Pub. No.: WO2022/003598
PCT Pub. Date: Jan. 6, 2022

(65) Prior Publication Data
US 2023/0226050 A1 Jul. 20, 2023

Related U.S. Application Data

(60) Provisional application No. 63/047,513, filed on Jul. 2, 2020.

(51) Int. Cl.
| | |
|---|---|
| *A61K 31/4985* | (2006.01) |
| *A61K 31/505* | (2006.01) |
| *A61K 31/675* | (2006.01) |
| *A61P 31/18* | (2006.01) |

(52) U.S. Cl.
CPC ........ *A61K 31/4985* (2013.01); *A61K 31/505* (2013.01); *A61K 31/675* (2013.01); *A61P 31/18* (2018.01)

(58) Field of Classification Search
CPC ................................................. A61K 31/4985
See application file for complete search history.

(56) References Cited

U.S. PATENT DOCUMENTS

2020/0147079 A1     5/2020   Crauwels et al.

FOREIGN PATENT DOCUMENTS

| WO | WO 2016/196471 A1 | 12/2016 |
| WO | WO 2017/205585 A1 | 11/2017 |

OTHER PUBLICATIONS

Margolis et al. Lancet, 2017, 390(10101):1499-1510.*
Margolis et al. Lancet Infectious Diseases, 2015, 15(10): 1145-1155.*
Rajoli et al., Clinical Pharmacokinetics, 2018, 57(2): 255-266.*
McPherson et al., Expert Opinion on Investigational Drugs, 2018, 27(4): 413-420.*
Margolis David A et al: "Cabotegravir plus rilpivirine, once a day, after induction with cabotegravir plus nucleoside reverse transcriptase inhibitors in antiretroviral-naive adults with HIV-1 infection (LATTE): a randomised, phase 2b, dose-ranging trial", The Lancet Infectious Diseases Aug. 2013, vol. 15, No. 10, Oct. 1, 2015 (Oct. 1, 2015), pages pp. 1146, col. 2.
Henn Aurelia et al: "Primary HIV Infection: Clinical Presentation, Testing, and Treatment", Current Infectious Disease Reports, Current Science, Philadelphia, PA, US, vol. 19, No. 10, Sep. 7, 2017 (Sep. 7, 2017), pp. 1-10, XP036314716, ISSN: 1523-3847, DOI: 10.1007/S11908-017-0588-3 [retrieved on Sep. 7, 2017] pp. 4-6.
Daly M et al: "Infection outcome in RT-SHIV infected macaques treated early with antiretroviral therapy alone or in combination with the TLR7 agonist vesatolimod", Jul. 10, 2020 (Jul. 10, 2020), XP055842202, Retrieved from the Internet: URL:https://onlinelibrary.wiley.com/doi/fu ll/10.1002/jia2.25547 [retrieved on Sep. 17, 2021] the whole document.
"HIV: World Health Organization," Retrieved on Dec. 19, 2025, pp. 1-15, Retrieved from [https://www.who.int/health-topics/hiv-aids#tab=tab_1].

* cited by examiner

*Primary Examiner* — Rei Tsang Shiao
(74) *Attorney, Agent, or Firm* — William B. Stauffer

(57) ABSTRACT

A method of achieving HIV viral remission in a patient in need thereof, comprising the steps of:
after exposure of the patient to the HIV virus, administering an early antiretroviral therapy (eART) of therapeutically effective amounts of cabotegravir and rilpivirine long-acting antiretrovirals, and
after eART suppression of the virus, discontinuing said early antiretroviral therapy.

11 Claims, 6 Drawing Sheets

Figure 1:
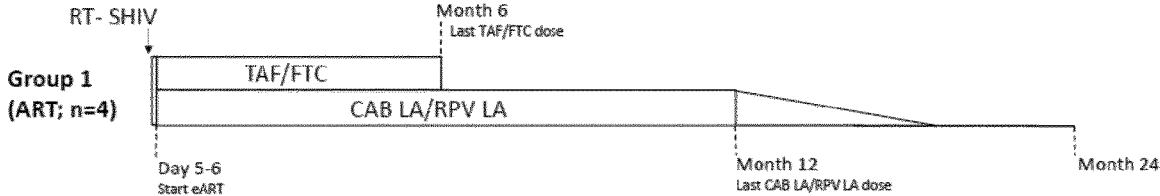
Figure 1:
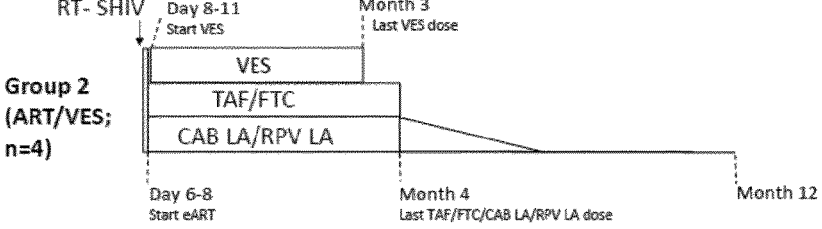

**Group 3
(untreated
Controls; n=2)**

1

METHOD OF ACHIEVING HIV VIRAL REMISSION USING LONG-ACTING ANTIRETROVIRAL AGENTS

CROSS REFERENCE TO RELATED APPLICATIONS

This application is a § 371 national phase entry of International Application No. PCT/IB2021/055874, filed 30 Jun. 2021, which claims the benefit of U.S. Provisional Application No. 63/047,513, filed 2 Jul. 2020.

STATEMENT REGARDING FEDERALLY SPONSORED RESEARCH

This invention was made with Government support under project number 1845 and Cooperative Research Agreement Number D-588-16 by the Centers for Disease Control and Prevention, National Center for HIV/AIDS, Viral Hepatitis, STD, and TB Prevention, Division of HIV/AIDS Prevention. The Government has certain rights in the invention.

FIELD OF THE INVENTION

The invention relates to the prevention or treatment of Human Immunodeficiency Virus (HIV) infection. In particular, the invention relates to a process for achieving partial or complete remission of an HIV infection where treatment is initiated early with a combination regimen containing long-acting antiretroviral drugs with or without a latency reversal agent.

BACKGROUND TO THE INVENTION

Among viruses, human immunodeficiency virus (HIV), a kind of retrovirus, is known to cause acquired immunodeficiency syndrome (AIDS). Potent, combination antiretroviral therapy (cART) has revolutionized the care of pateints with HIV infection. Cure of the HIV infection, such that cART would no longer be required, has been elusive because of the persistence of both low-level viremia and a long-lived reservoir of latently-infected cells mostly consisting in memory $CD4_+$ T cells with proviruses capable of being activated to produce infectious viruses. Hong F F. *AIDS Rev.* 2015; 17 (2): 71-82.

It has been general practice to defer the initiation of antiretroviral therapy in asymptomatic patients with a $CD4_+$ count above a certain threshold level. De Cock K M., *N Engl J Med* 2013; 368:886-889. The effect of the timing of the initiation of antiretroviral therapy on clinical and microbiologic outcomes has been controversial in evaluations of the benefit of therapy and of the associated short- and long-term complications and costs. For many years, antiretroviral therapy was delayed until a patient's $CD4_+$ count fell below 200 cells per cubic millimeter, which led to frequent opportunistic infections. Severe P., *N Engl J Med.* 2010 Jul. 15; 363 (3): 257-65. Retrospective analyses of patients with HIV-1 infection who were treated in developed countries have suggested a benefit from early antiretroviral therapy (eART). Cohen M S., *N Engl J Med.* 2011; 365 (6): 493-505. These data, along with observational studies, provide strong evidence for the initiation of antiretroviral therapy in patients with higher $CD4_+$ cells per cubic millimeter. Lundgren J., *N Engl J Med.* 2016; 374 (4): 394.

Achieving a combination antiretroviral therapy that is administered at an early antiretroviral therapeutic time point and reduces low-level viremia and the reservoir of latently-infected cells is desirable. Combination antiretrovial therapy has yet to find the composition that accomplishes the above mentioned criteria that would ultimately result in a patient being able to stop antiretroviral therapy either through remission or cure.

As such, there is a need in the art for an antiretroviral therapy that effectively treats HIV by further reducing low-level viremia and the latent reservoir of $CD4_+$ cells that are capable of reintroducing infectious virus into the host.

SUMMARY OF THE INVENTION

Methods are disclosed herein for achieving virologic remission (also referred to as functional cure) in a primate host infected by an immunodeficiency virus without the necessity of continued treatment with antiviral agents. Remission is demonstrated by the lack of virus rebound in plasma after discontinuation of suppressive antiretroviral therapy. Remission is achieved when treatment is initiated within days or weeks after acute exposure with a combination regimen that contains long-acting antiretroviral (ARVs) drugs. Here, we demonstrate virologic remission with a combination regimen containing a pharmacologically effective amount of the integrase inhibitor cabotegravir long-acting (CAB-LA), and a pharmacologically effective amount of the nonnucleoside reverse transcriptase inhibitor rilpivirine long-acting (RPV-LA). Treatment is effective if initiated within days or weeks after acute exposure. In the specific description, virus remission is achieved when treatment is discontinued after a period of sustained viral suppression. The discovery informs a new biomedical approach to achieving functional virologic remission and potentially cure of HIV.

Early antiretroviral therapy or eART improves clinical outcomes by reducing the size and diversity of the viral reservoir, limiting immune damage and delaying viral rebound after treatment interruption. Latency reversing agents, or LRAS, activate the viral reservoir. Virally suppressed individuals have been treated with LRAs in attempt to purge latent virus for the 'shock and kill' strategy, which so far has not been clinically successful. The use of LRAs during acute infection has not been evaluated. Here, we show that clinical outcomes of eART can be improved using long acting antiretroviral drugs. These formulations have a prolonged drug tail which may further delay viral rebound, potentially leading to a chemovaccination effect. Second, we show that adding an LRA to an eART regimen can reduce viral reservoir formation by purging it during early infection and stimulating a stronger immune response.

According to an embodiment, there is provided a method of achieving HIV viral remission in a patient in need thereof, comprising the steps of, after infection of the patient with HIV, administering an early antiretroviral therapy (eART) of therapeutically effective amounts of cabotegravir and rilpivirine long-acting antiretrovirals, and, after eART suppression of the virus, discontinuing said early antiretroviral therapy.

According to an embodiment, the early antiretroviral therapy is initiated at a pre-determined time after infection of the patient with HIV. According to another embodiment, the early antiretroviral therapy is initiated while the patient has a subject has >500$CD4_+$ cells/ml.

According to another embodiment, early antiretroviral therapy further comprises administration of at least one or more additional antiretroviral agents. The one or more additional antiretroviral agents may comprises emtricitabine (FTC) and/or tenofovir or a prodrug thereof.

According to another embodiment, the method of achieving HIV viral remission further comprises administration of a latency reversing agent. In one embodiment, the latency reversing agent is a TLR7 agonist. An exemplary TLR7 agonist is vesatolimod.

According to an embodiment, there is provided cabotegravir and rilpivirine long-acting antiretrovirals for use as early antiretroviral therapy (eART) in achieving viral remission in a patient in need thereof.

DESCRIPTION OF DRAWINGS/FIGURES

FIG. 1 is a graph that describes the experimental design. Rhesus macaques (=10) were infected rectally with a single high dose of pathogenic RT-SHIV isolate containing a T to C substitution at position 8 of the SIV tRNA primer binding site that improves virus replication and increases pathogenicity. Macaques in Group I (n=4) initiated treatment with CAB-LA/RPV-LA/FTC/Tenofovir alafenamide (TAF) at day 5/6 post virus inoculation and confirmation of infection infection by RT-SHIV RNA detection in plasma. Treatment with CAB-LARPV-LA/FTC/TAF was maintained for 6 months followed by a simplified regimen with CAB LA/RPV LA for 6 additional months. All treatment was discontinued at month 12. Macaques in Group II (n=4) initiated treatment with CAB-LA/RPV-LA/FTC/TAF at day 6/8 after infection with the addition of weekly VES treatment at day 8-11. VES treatment was discontinued at month 3 and CAB-LA/RPV-LA/FTC/TAF was stopped at month 4. Macaques in Group III (n=2) are untreated controls.

Figure 2:
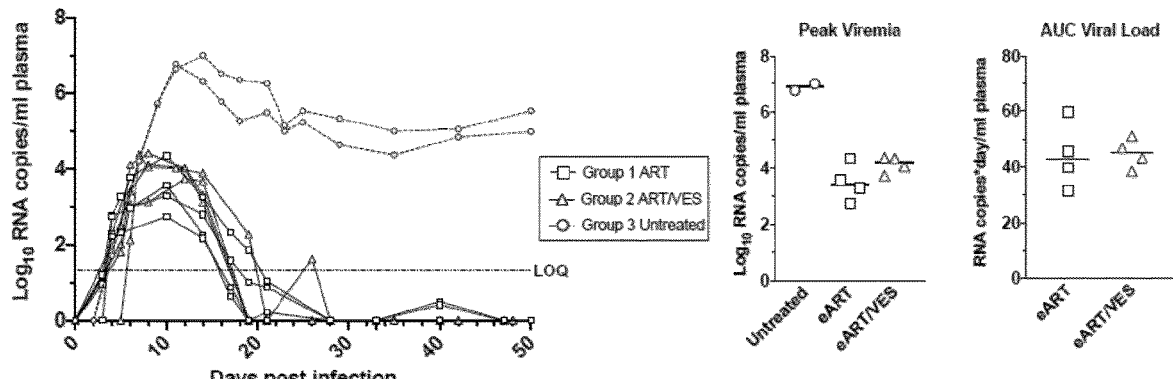

FIG. 2 is a graph that describes the dynamics of virus replication during the first 50 days of infection as expressed as $\log_{10}$ RNA copies of SHIV RNA in plasma. The horizontal dotted line denotes the lower limit of quantification of the SHIV RNA assay (12.5 copies/ml of plasma). Plasma SHIV RNA levels during early acute infection were significantly reduced in Group I and Group II compared to the untreated controls in Group III. Peak viremia in Groups I and II were similar (3.4 [range=2.7-4.3] and 4.2 [3.7-4.4] log 10 RNA copies/ml, p=0.111) and lower than the untreated controls (6.8-7.0 log 10RNA copies/ml). Virus replication from treatment initiation until virus suppression was also similar in Group I and Group II animals (AUC viral load=42.6 [31.6-59.7] and 45.0 [38.4-51.07] RNA copies/ml/day, p=0.886), although Group II animals suppressed replication earlier (18 [14-22] vs. 13 [11-13] dpi, p=0.029).

Figure 3:
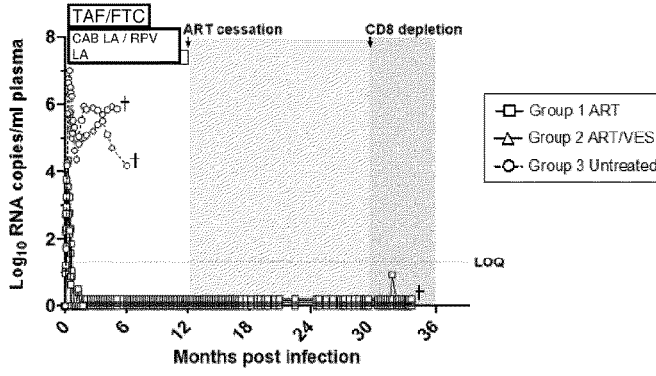
Figure 3:
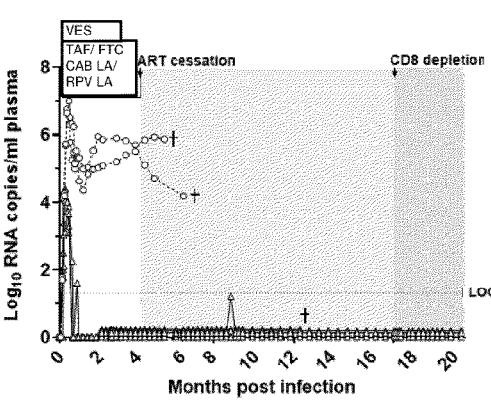

FIG. 3 is a graph that describes the dynamics of virus replication during the entire treatment period and after treatment cessation. All the animals from Group I had undetectable virus in plasma during the 12 months of treatment and remain aviremic after treatment cessation and a follow up period of 22 months (months 12 to 34) that included transient depetion of CD8 positive cells from blood. Likewise, all the animals from Group II had undetectable virus in plasma during the 4 months of treatment and remain aviremic after treatment cessation and a follow up period of 16 months (months 4-20) that included a transient depletion of CD8 positve cells from blood.

Figure 4:
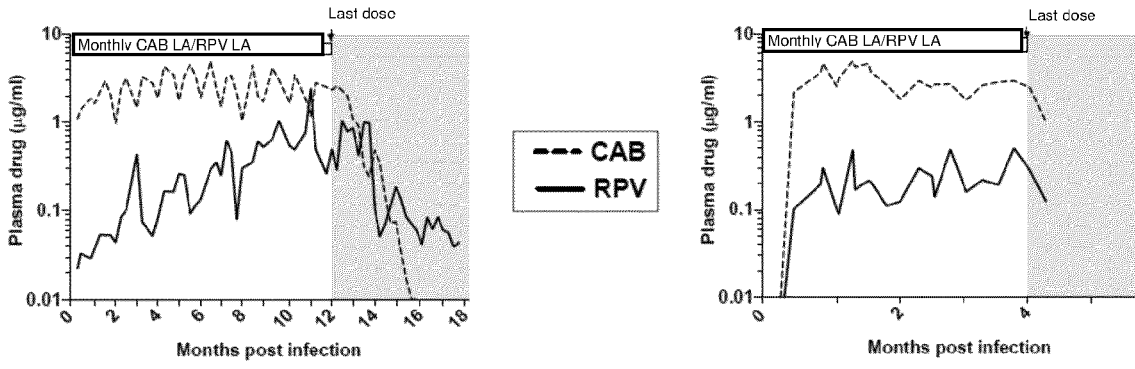

FIG. 4 is a graph that describes the concentrations of CAB and RPV in plasma during the entire treatment period and after treatment cessation. After the last dose concentrations of CAB and RPV declined over 4-7 months to undetectable levels. No virus rebound was observed during this drug tail and up to 4-5 months afterwards.

Figure 5:
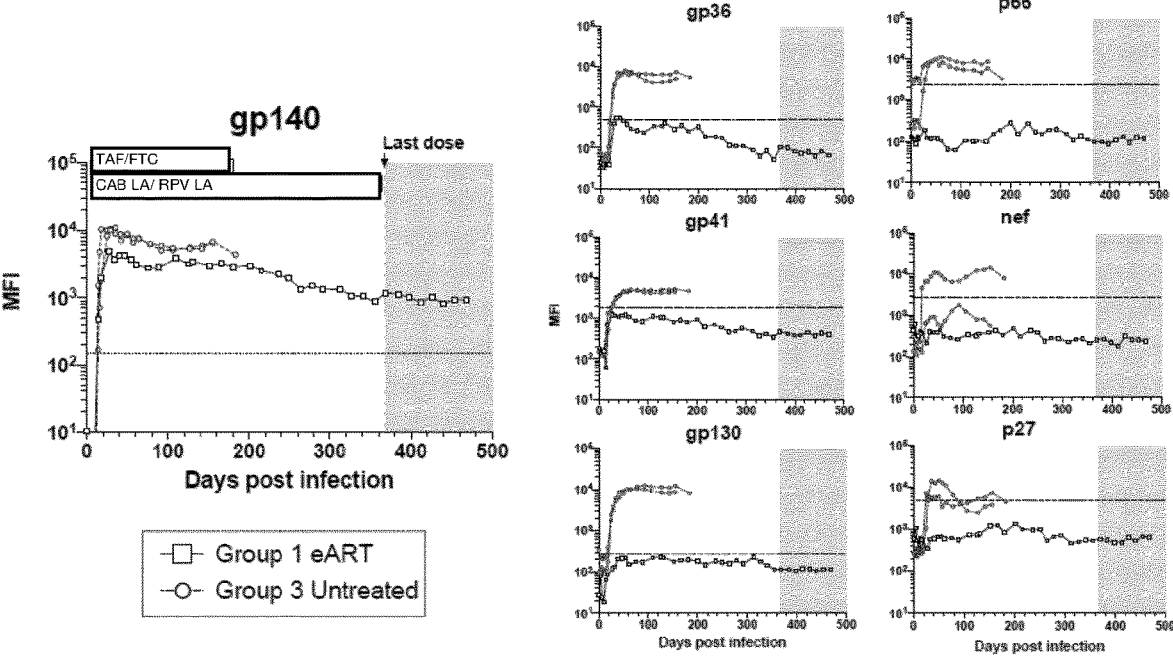
Figure 6:
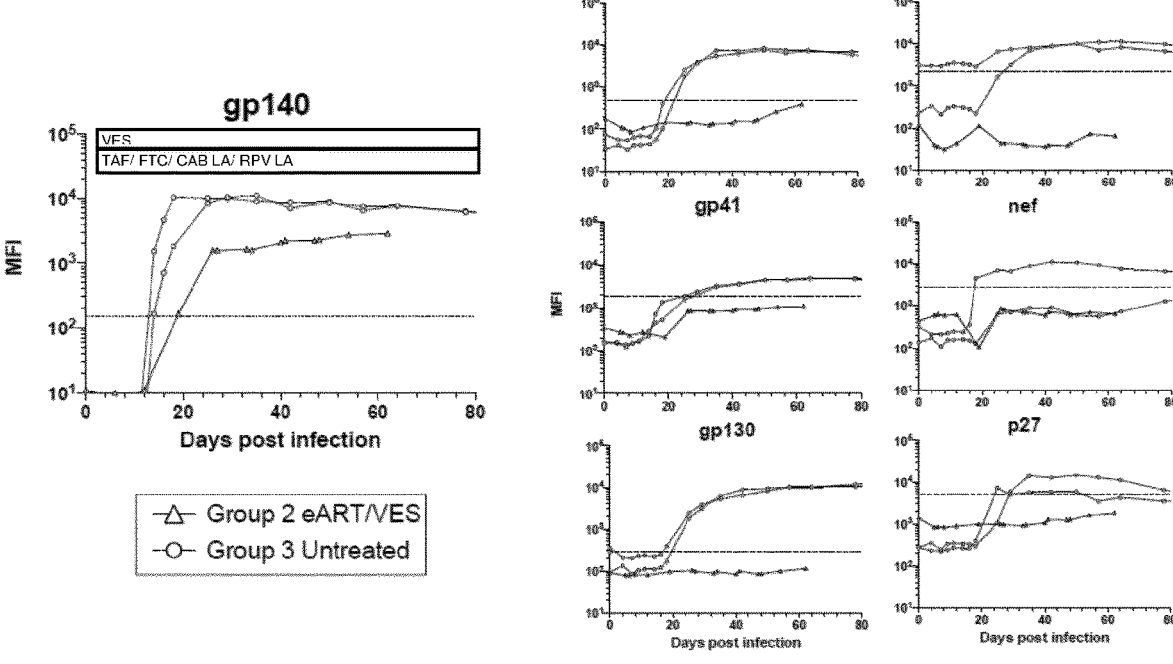

FIGS. 5 and 6 are graphs that describe antibody responses to p66, gp130, gp41, nef, gp36, gp140, and p27. Serologic responses in untreated controls were observed for the full panel tested. In contrast, responses in Group I (FIG. 5) and II (FIG. 6) were limited primarily to gp140, albeit they developed at different rates (14 [14-17] vs. 36.5 [33-40] days post-infection, respectively, p=0.029).

DETAILED DESCRIPTION OF THE INVENTION

Definitions

As used herein, "pharmaceutical composition" or "pharmaceutical compositions" refers to a combination described herein and at least one pharmaceutically acceptable carrier or adjuvant. The term "pharmaceutically acceptable carrier or adjuvant" refers to a carrier or adjuvant that may be administered to a patient, together with a combination of this invention, and which does not destroy the pharmacological activity thereof and is nontoxic when administered in doses sufficient to deliver a therapeutic amount of the antiviral agent.

Examples of pharmaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product. The present invention further includes a pharmaceutical composition as hereinbefore defined wherein a compound of the present invention or a pharmaceutically acceptable derivative thereof and another therapeutic agent are presented separately from one another as a kit of parts.

In one particular embodiment, exemplary pharmaceutical compositions are those suitable for parenteral administration and include aqueous and nonaqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described. Unit dosage pharmaceutical compositions include those containing a daily dose or daily subdose of the active ingredients, as hereinbefore recited, or an appropriate fraction thereof.

As used herein "patient" or "subject" refers to mammals and includes humans and non-human mammals.

As used herein, "treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Accordingly, in one aspect, there is provided a method of treating an HIV infection in a subject comprising administering to the subject a combination as described herein, or pharmaceutically acceptable salts thereof. There is also provided, in another aspect, a combination for use in treating an HIV infection. There is also provided, in another aspect, the use of a combination in the manufacture of a medicament for treating an HIV infection.

Accordingly, in one aspect, there is provided a method of preventing an HIV infection in a subject comprising administering to the subject a combination as described herein, or pharmaceutically acceptable salts thereof. There is also provided, in another aspect, a combination for use in preventing an HIV infection. There is also provided, in another aspect, the use of a combination in the manufacture of a medicament for preventing an HIV infection.

As used herein "latency" means a concept describing 1) the dormant state of viral activity within a population of cells, wherein viral production, viral packaging, and host cell lysis does not occur, or occurs at a very low frequency, or 2) the down-regulation or absence of gene expression within an infected cell. As used herein, "reversing latent HIV infection" refers to a treatment that upregulates the expression of integrated HIV genomes within latently infected cells, such, as a non-limiting example, as the compounds(s) that may activate the non-canonical NF-kB pathway, leading to susceptibility of the infected cell to virally-induced cell death or immunologic clearance. As used herein, "depleting latent HIV infection" refers to the clearance of latently HIV-infected cells that may follow the reversal of HIV latency by reagents such as those that activate the non-canonical NF-kB pathway.

Accordingly, in one aspect, the invention provides a method of depleting latent HIV infected cells comprising administering to a subject a combination described herein, or pharmaceutically acceptable salts thereof. There is also provided, in another aspect, a combination for use in depleting latent HIV infected cells. There is also provided, in another aspect, the use of a combination in the manufacture of a medicament for treating an HIV infection.

As used herein, "virologic remission" or "functional cure" refers to the eradication, stoppage, halt or end of the human immunodeficiency virus or symptoms, or the progression of the symptoms or virus, for a defined period. As an example, in one embodiment, "virologic remission" or "functional cure" refers to a therapeutic combination of administrations that alone or in combination with one or more other compounds induces and maintains sustained viral control (undetectable levels of plasma viremia by, e.g., a polymerase chain reaction (PCR) test, a bDNA (branched chain DNA) test or a NASBA (nucleic acid sequence based amplification) test, collectively "undetectable"), of human immunodeficiency virus after a minimum of 3 months without any other therapeutic intervention. The above PCR, bDNA and NASBA tests are carried out using techniques known and familiar to one skilled in the art. As another example, in one embodiment, "virologic remission" or "functional cure" refers to a therapeutic combination of administrations that alone or in combination with one or more other compounds induces and maintains sustained viral control defined as maintenance of less than 50 copies/mL of HIV viral RNA as determined by a suitable test throughout and then after a minimum of 3 months without any other therapeutic intervention.

In another embodiment virus is undectable for a minimum of 6 months without any other therapeutic intervention. In another embodiment virus is undectable for a minimum of, alternatively, 12 or 18 months without any other therapeutic intervention. In another embodiment virus is undectable for a period up to 2 years without any other therapeutic intervention.

In another embodiment viral load is maintained below 50 copies/mL for a minimum of 6 months without any other therapeutic intervention. In another embodiment viral load is maintained below 50 copies/mL for a minimum of, alternatively, 12 or 18 months without any other therapeutic intervention. In another embodiment viral load is maintained below 50 copies/mL for a period up to 2 years without any other therapeutic intervention.

As used herein, "cure" or "curing" a disease in a patient is used to denote the eradication, stoppage, halt or end of the human immunodeficiency virus or symptoms, or the progression of the symptoms or virus, for a defined period. As an example, in one embodiment, "cure" or "curing" refers to a therapeutic combination of administrations that alone or in combination with one or more other compounds induces and maintains sustained viral control (undetectable levels of plasma viremia by, e.g., a polymerase chain reaction (PCR) test, a bDNA (branched chain DNA) test or a NASBA (nucleic acid sequence based amplification) test), of human immunodeficiency virus after a minimum of two years without any other therapeutic intervention. The above PCR, bDNA and NASBA tests are carried out using techniques known and familiar to one skilled in the art. As an example, the eradication, stoppage, halt or end of the human immunodeficiency virus or symptoms, or the progression of the symptoms or virus, may be sustained for a minimum of two years.

Accordingly, in one aspect, the invention provides a method of curing an HIV infection in a subject comprising administering to the subject a combination as described herein. There is also provided, in another aspect, a combination for use in curing an HIV infection. There is also provided, in another aspect, the use of a combination in the manufacture of a medicament for curing an HIV infection.

"Early antiretroviral therapy" or "eART" is a method of improving clinical outcomes by initiating antiretroviral treatment soon enough after infection with HIV that opportunity for the virus to establish a viral reservoir of size and diversity is diminished. Established benefits of eART also include limitation on immune system damage and delay in time to viral rebound. Viral reservoirs include latently infected cells and virus in immunologically privileged tissue sites, that are highly, if not completely, resistant to clearance by combination antiretroviral therapy (cART) or any natural immunologic mechanism (Okoye et al., Nat Med. 2018 September; 24 (9): 1430-1440). According to one embodiment, eART is characterized by the quantity of an individual's CD4 cells per cubic millimeter (ml) remaining immediately prior to initiation of ART. According to another embodiment, eART is characterized simply by time of delay between HIV exposure and initiation of ART.

"Antiretroviral therapy" or "ART" is the therapeutic treatment for HIV infection involving administration of at least one anti-retroviral agent (e.g., one, two, three or four anti-retroviral agents) to an HIV-infected (or HIV-exposed) individual during a course of treatment.

Early Antiretroviral Treatment (eART)

In some embodiments, one or more antiretroviral agents are administered or co-administered to a subject at specific time points, such as within 12 hours, 24 hours, 48 hours, 3 days, 4 days, 5 days, 6 days, 7 days, 8 days, 9 days, 10 days, 11 days, 12 days, 13 days, or 14 days.

In some embodiments, one or more antiretroviral agents are administered or co-administered to a subject before depletion of CD4$_+$ cells. For instance, eART may be initiated while a subject has >500CD4$_+$ cells/ml. eART may be initiated while a subject has >350 CD4$_+$ cells/ml. eART may be initiated while a subject has >200 CD4$_+$ cells per ml.

In an embodiment, eART comprises the combined regimen of cabotegravir and rilpivirine. Subjects may be dosed according to current clinical regimens specified for use of the ART agents. For instance, subjects may receive 30 mg of oral cabotegravir plus 25 mg of rilpivirine once daily for an introductory period (e.g. the first 4 weeks). Alternatively, initially or after the introductory period, subjects may receive initial doses of 600 mg of cabotegravir and 900 mg of rilpivirine (a 3-ml injection of each drug) by IM injection, followed by injections of 400 mg of cabotegravir and 600 mg of rilpivirine (a 2-ml injection of each drug) every 4 or 8 weeks until ART treatment is discontinued. Of course, the cabotegravir and rilpivirine ART regimen may be weight adjusted or otherwise meaningfully adjusted as clinically appropriate.

In another embodiment, cabotegravir and rilpivirine eART specified above is provided in conjunction with one or more additional antiretroviral agents. The purpose of one or more additional antiretroviral agents is to ensure complete initial suppression of HIV virus upon initiation of eART treatment. Suitable additional agents may include NRTIs and/or NtRTIs.

In order to be incorporated into the viral DNA, nucleoside analog reverse-transcriptase inhibitors (NRTIs) must be activated in the cell by the addition of phosphate groups to their deoxyribose moiety, to form NRTI triphosphates. This phosphorylation step is carried out by cellular kinase enzymes. NRTIs include zidovudine, didanosine, zalcitabine, stavudine, lamivudine, abacavir, and emtricitabine (also called FTC).

Nucleotide analog reverse-transcriptase inhibitors (NtRTis): NTARTis and NtRTis are nucleotide analogues of cytidine, guanosine, thymidine, and adenosine that are of use in treatment of HIV infections. For example, tenofovir (including prodrugs TDF and TAF) is an NtRTI adenosine analogue.

According to an embodiment, eART comprises treatment with cabotegravir and rilpivirine, along with FTC and TAF. According to another embodiment, the eART comprises treatment with cabotegravir and rilpivirine, along with FTC and TAF administered as 200 mg/day FTC and 10 mg/day TAF during the eART period.

TLR Modulators

A "TLR modulator" is an agent that functionally interacts with a TLR expressed in a mammalian cell (e.g., a human cell). In some embodiments, the modulator is a TLR agonist. In some embodiments, the modulator is a TLR antagonist. In some embodiments, the modulator is an agent that is selective for TLR7. In some embodiments, the modulator is an agent that is selective for TLR7 and one or more TLRs, such as TLR8.

TLR Agonists

The term "TLR agonist" is an agent that binds to and activates a TLR expressed in a mammalian cell (e.g., a human cell). In some embodiments, the TLR agonist binds to and activates TLR7. Non-limiting examples of TLR agonists are described in Bhardwaj et al., *Cancer J.* 16 (4): 382-391, 2010; Meyer et al., *Exp. Opin. Investig. Drugs* 17 (7): 1051-1065, 2008; Adams, *Immunotherapy* 1 (6): 949-

964, 2009; Hennessy et al., *Nat. Rev. Drug Discov.* 9:293-307, 2010; and U.S. Pat. Nos. 7,498,409; 9,421,254; 8,409,813; 8,361,986; 8,795,678; 8,728,486; 8,636,979; 8,999,946; 9,359,360; 9,050,376; and 9,556,167; US 2014/0322271; US 2016/0206690; US 2009/0253622; US 2011/0135669; US 2011/0250175; US 2014/0220074; and US 2012/0219615; each incorporated in its entirety herein. In some embodiments, the TLR agonist is a peptide or a fusion protein (Huleatt et al., *Vaccine* 25:763-775, 2007).

In some embodiments, the TLR agonist is administrated in combination with another composition (Dowling et al., *Clin. Transl. Immunol.* 5: e85, 2016). In some embodiments, the TLR agonist is an endogenous molecule released from dead cells (e.g., a heat shock protein (HSP) and mobility group box 1 (HMGB1); Asea et al., *J. Biol. Chem.* 277: 15028-15034, 2002; Kepp et al., *Cancer Metastasis* 30:61-69, 2011).

TLR7 Agonists

In some embodiments, the TLR agonist is vesatolimod (formerly known as GS-9620). In some embodiments, the TLR agonist is ANA975 (isotorabine) (Anadys/Novartis), ANA773 (Anadys/Novartis). In some embodiments, the TLR7 agonist is an imidazoquinoline or a variant thereof (e.g., imiquimod (Aldara. T M.; Kaspari et al., *British J. Dermatology* 147:757-759, 2002; Smorlesi et al., *Gene Therapy* 12:1324-133, 2005; Prins et al., *J. Immunol.* 176: 157-164, 2006; Shackleton et al., *Cancer Immun.* 4:9, 2004; Green et al., *Br. J. Dermatol.* 156 (2): 337-345, 2007; Geisse et al., *Am. Acad. Dermatol.* 50 (5): 722-733, 2004; Wolf et al., *Arch. Dermatol.* 139 (3): 273-276, 2003), resiquimod (R848; Hemmi et al., *Nat. Immunol.* 3:196-200, 2002; Jurk et al., *Nat. Immunol.* 3:49, 2002; Rook et al., *Blood* 126 (12): 1452-1461, 2015; Dovedi et al., *Blood* 121:251-259, 2013). In some embodiments, the TLR agonist is a synthetic imiadzoquinoline mimicking viral single stranded RNA (ssRNA) (852A) or a variant thereof (Dudek et al., *Clin. Cancer Res.* 13 (23): 7119-7125, 2007; Dummer et al., *Clin. Cancer Res.* 14 (3): 856-864, 2008; Weigel et al., *Am. J. Hematol.* 87 (10): 953-956, 2012; Geller et al., *Cancer Immunol. Immunother.* 59 (12): 1877-1884, 2010; Inglefield et al., *J. Interferon Cytokine Res.* 28 (4): 253-263, 2008). In some embodiments, the TLR agonist is a small molecule. In some embodiments, the small molecule mimics viral ssRNA (e.g., motolimod (VTX-2337)) or a variant thereof (Dietsch et al., *Clin. Cancer Res.* 21 (24): 5445-5452, 2015; Northfelt et al., *Clin. Cancer Res.* 20 (14): 3683-3691, 2014; Lu et al., *Clin. Cancer Res.* 18 (2): 499-509, 2012). In some embodiments, the small molecule is GS-9620 or a variant thereof (Bam et al., *Antimicrob Agents Chemother.* 61 (1): e01369, 2016; Rebbapragada et al., *PLOS One* 11 (1): e0146835, 2016; Gane et al., *J. Hepatol.* 63 (2): 320-328, 2015; Fosdick et al., *J. Med. Chem.* 56 (18): 7324-7333, 2013). In some embodiments, the small molecule is SC1 (Wiedemann et al., *Oncoimmunology* 5 (7): e1189051, 2016; Hamm et al., *J. Immunol.* 6 (4): 257-265, 2009). In some embodiments, the small molecule is gardiquimod (Ma et al., *Cell. Mol. Immunol.* 7:381-388, 2010; Hjelm et al., *Hum. Vaccin. Immunother.* 10 (2): 410-416, 2014; Buitendijk et al., *AIDS Res. Hum. Retroviruses* 29 (6): 907-918, 2013), CL075 (Philbin et al., *J. Allergy Clin. Immunol.* 130:195-204, 2012; Dowling et al., *PLOS One* 8 (3): e58164, 2013), CL097 (Gorden et al., *J. Immunol.* 174:1259-1268, 2005; Gorski et al., *Int. Immunol.* 18:1115, 2006; Levy et al., *Blood* 108:1284-1289, 2006; Wille-Reece et al., *J. Exp. Med.* 203:1249-1258, 2006), loxoribine (Pope et al., *Cell Immunol.* 162:333, 1995; Heil et al., *Eur. J. Immunol.* 33:2987-2997, 2003; Lee et al., *PNAS* 100:6646-6651, 2003), or VTX-294 (Dowling et al.,

9

*PLOS One* 8 (3): e58164, 2013). In some embodiments, the TLR7 agonist is IMO-9200. In some embodiments, the TLR7 agonist is IPH-32XX (Innate Pharma).

According to another embodiment, the method of achieving HIV viral remission further comprises administration of a latency reversing agent. In one embodiment, the latency reversing agent is a TLR7 agonist. An exemplary TLR7 agonist is vesatolimod.

EXAMPLES

We investigated in 8 macaques the kinetics of virus suppression after early treatment initiation with a combination of CAB-LA, RPV-LA, FTC, and TAF, with or without the immunomodulator VES, and defined dynamics of virus rebound after treatment cessation and show in all 8 animals durable absence of virus rebound. Previous work in similar macaque models of early treatment with suppressive antiretroviral regimens containing daily administration of drugs like tenofovir, emtricitabine, and dolutegravir have resulted in little or no remission (Okoye et al., Nat Med 2018; Whitney et al., Nature 2014; Whitney et al., Nat Comm 2018; Namazi et al., J Infec Dis 2018). Thus, the regimen and methods described here which include long-acting ARVs have superior ability to induce remission. This potent regimen contains long-acting ARV drugs that provide prolonged antiviral activity and can potentially induce a chemovaccination effect after treatment cessation.

Example 1

Antiretroviral Drug Doses

Doses of 50 mg/kg CAB LA and 200 mg/kg RPV were administered intramuscularly once a month. These doses result in plasma CAB and RPV concentrations that are well above their respective protein-adjusted concentrations required for 90% viral inhibition (0.166 ug/ml and 12 ng/ml), and within the range of those seen in humans (Andrews et al., Science 2014; Melody et al., AAC 20150. Doses of TAF (1.5 mg/kg) and FTC (20 mg/kg) were administered with food once a day, except subcutaneously on the days of specimen collection or if animals did not eat their entire oral dose. The doses of FTC and TAF result in plasma and intracellular drug concentrations that are within the range of those achieve in humans (Massud et al., J Infect Dis 2016).

Example 2

Virus Inoculations And Treatment Regimens

Macaques were infected with a chimeric RT-SHIV isolate that contains the reverse transcriptase of HIV-1 clone HXBc2 in a background of SIVmac239. RT-SHIV contains a T to C substitution at position 8 of the SIV tRNA primer binding site that improves replication (Soderberg et.al., 2002) and was obtained from the National Institutes of Health (NIH) AIDS Research and Reference Reagent Program. Macaques were infected with a single dose of RT-SHIV (10ˆ 3.3 TCI D50) intrarectally. Blood draws were collected longuitudinally to monitor infection status and drug cocentrations. FIG. 1 shows the study design and the interventions evaluated in each group of animals. Macaques in Group I (n=4) initiated treatment with CAB-LA/RPV-LA/FTC/TAF at day 5/6 after infection. Treatment with CAB-LA/RPV-LA/FTC/TAF was maintained for 6 months followed by a simplified regimen with CAB LA/RPV LA for 6 additional months. All treatment was discontinued at month 12. Macaques in Group II (n=4) initiated treatment with CAB-LA/RPV-LA/FTC/TAF at day 6/8 after infection with the addition of weekly VES treatment at day 8-11. VES treatment was discontinued at month 3 and CAB-LA/RPV-LA/FTC/TAF was stopped at month 4. Macaques in Group III (n=2) are untreated controls. SHIV RNA in plasma was monitored by an RT-PCR assay with a limit of quantification of 12.5 RNA copies per ml of plasma.

Example 3

Acute SHIV Infection Dynamics

FIG. 2 shows that all 8 animals in the treatment arms rapidly achieved undetectable SHIV RNA levels in plasma within 20-25 days of infection. Peak SHIV RNA concentrations in Groups I and II animals were similar (3.4 [range=2.7-4.3] and 4.2 [3.7-4.4] log 10 RNA copies/ml, p=0.111) and lower than the untreated controls (6.8-7.0 log 10RNA copies/ml). Virus replication from treatment initiation until virus suppression as defined by the area under the curve (AUC) value was also similar in Group 1 and Group 2 animals (AUC=42.6 [31.6-59.7] and 45.0 [38.4-51.07] RNA copies/ml/day, p=0.886), although Group II animals suppressed replication earlier (18 [14-22] vs. 13 [11-13] dpi, p=0.029). Thus, the regimen containing CAB-LA/RPV-LA/FTC/TAF with or without VES was able to rapidly suppress virus replication within 3-4 weeks of treatment.

Example 4

Infection Outcome During Prolonged Treatment and after Treatment Discontinuation SHIV RNA concentrations in plasma were monitored every one or two weeks during the entire treatment phase of the study and remained below the limit of detection of the assay in all 8 treated animals from Groups I and II at every time point tested (FIG. 3). During the 3 months of VES treatment in Group II animals, plasma samples were also collected 24 hrs after the weekly VES dose; no viral blips were detected in any macaque at any of the time points tested.

Treatment with CAB-LA/RPV-LA/FTC/TAF in Group I animals was stopped at month 12. FIG. 3 shows that SHIV RNA levels in plasma remained undetectable in all 4 animals 22 months after treatment discontinuation despite transient depletion of CD8 positive cells from blood. Treatment with VES in Group II animals was stopped at month 3 and treatment with CAB-LA/RPV-LA/FTC/TAF was stopped one month later. FIG. 3 shows that SHIV RNA levels in plasma remained undetectable in all 4 animals 16 months after the last treatment, with the exception of one animal that showed a transient blip at month 5. Transient depletion of CD8 positive cells in these animals did not result in sustained virus rebound.

Example 5

Concentrations of CAB and RPV in Plasma

CAB and RPV concentrations in plasma were measured using an LC-MS method with a lower limit of quantification of 10 ng/ml. The concentrations of CAB and PRV in plasma during the entire treatment period and after the last dose are shown in FIG. 5. Concentrations of CAB and RPV remained detected in plasma 4-7 months after the last dose highlighting the persistence of these two antivirals for several months after treatment cessation. Therefore, the prolonged persistence of CAB and RPV in plasma after treatment discontinuation was associated with virus remission and a chemovaccination effect.

Example 6

Virus Specific Antibody Responses

Antibody responses to p66, gp130, gp41, nef, gp36, gp140, and p27 were measured using an SIV/HIV Bio-Plex assay. Serologic responses in untreated controls from Group III were observed for the full panel tested. In contrast, responses in Groups I and II were limited to gp140, albeit they developed at different rates (14 [14-17] vs. 36.5 [33-40] days post-infection, respectively, p=0.029) (FIGS. 5 and 6).

Summary Example

Background: Early antiretroviral therapy (eART) preserves immune function and limits virus diversification but is not curative in people due to rapid viral reservoir establishment. We modeled in macaques the effect of a potent eART regimen [emtricitabine/tenofovir alafenamide (FTC/TAF) and long-acting cabotegravir/rilpivirine (CAB-LA/RPV-LA)] with or without the TLR7 agonist vesatolimod (VES).

Methods: Eight rhesus macaques infected intrarectally with RT-SHIV initiated treatment with human-equivalent doses of oral FTC/TAF (20 and 1.5 mg/kg daily) and intramuscular CAB-LA/RPV-LA (50 and 200 mg/kg monthly) at 6 (range=5-8) days post-infection (dpi). Group I (n=4) was treated for 12 months. Group II (n=4) was treated for 4 months and also received weekly VES (0.15 mg/kg). Two untreated animals were used as controls. Plasma viremia was monitored by RT-PCR (limit of quantification=50 copies). Antibody responses to p66, gp130, gp41, nef, gp36, gp140, and p27 were measured using an SIV/HIV Bio-Plex assay. The wilcoxon rank sum test was used to compare medians.

Results: Peak viremia in the eART-only and eART+ VES groups were similar (3.4 [range=2.7-4.3] and 4.2 [3.7-4.4] $\log_{10}$ RNA copies/ml, p=0.111) and lower than the untreated controls (6.8-7.0 $\log_{10}$ RNA copies/ml). Virus replication from treatment initiation until virus suppression was similar in the eART-only and eART$_+$ VES animals (AUC=42.6 [31.6-59.7] and 45.0 [38.4-51.07] RNA copies/ml/day, p=0.886), although eART$_+$ VES suppressed replication earlier (18 [14-22] vs. 13 [11-13] dpi, p=0.029). All macaques from the eART-only group had undetectable viremia during treatment and remain aviremic 10 months after treatment interruption. Serologic responses in untreated controls were observed for the full panel tested. In contrast, responses in the eART and eART+ VES groups were limited to gp140, albeit they developed at different rates (14 [14-17] vs. 36.5 [33-40] days post-infection, respectively, p=0.029). The eART-VES animals are currently undergoing treatment interruption.

Conclusions: Using a relevant macaque model of mucosal infection we show that potent early ART leads to prolonged viral control after treatment interruption. Serologic responses, limited to gp140, were consistent with efficient virus control. The combination of eART and VES quickly suppressed viremia and delayed serologic responses. Further characterization of immune function and virus dynamics will shed light on the immunomodulatory effect of VES during acute infection.

What is claimed is:

1. A method of achieving HIV viral remission in a patient in need thereof, comprising the steps of:

after exposure of the patient to the HIV virus, administering to said patient an early antiretroviral therapy (eART) of therapeutically effective amounts of cabotegravir and rilpivirine long-acting antiretrovirals, and after eART suppression of the HIV virus, discontinuing said early antiretroviral therapy.

2. The method of claim 1, wherein the early antiretroviral therapy is initiated within 2 weeks after exposure of the patient to the HIV virus.

3. The method of claim 1, wherein the early antiretroviral therapy is initiated while the patient has >500CD4+ cells/ml.

4. The method of claim 1, wherein early antiretroviral therapy further comprises administering one or more additional antiretroviral agents.

5. The method of claim 4, wherein the one or more additional antiretroviral agents comprises emtricitabine (FTC) and/or tenofovir or a prodrug thereof.

6. The method of claim 4, wherein early antiretroviral therapy further comprises administering to said patient a latency reversing agent.

7. The method of claim 6, wherein said latency reversing agent is a TLR7 agonist.

8. The method of claim 7, wherein the TLR7 agonist is vesatolimod.

9. A method of achieving HIV viral remission in a patient in need thereof comprising administering to said patient early antiretroviral therapy (eART) of cabotegravir and rilpivirine long-acting antiretrovirals.

10. The method of claim 1, wherein the early antiretroviral therapy is initiated while the patient has >350CD4+ cells/ml.

11. The method of claim 1, wherein the early antiretroviral therapy is initiated while the patient has >200CD4+ cells/ml.

* * * * *